(12) United States Patent
Shobana et al.

(10) Patent No.: US 6,723,844 B1
(45) Date of Patent: Apr. 20, 2004

(54) PREPARATION OF K-252A

(75) Inventors: Navayath Shobana, Grayslake, IL (US); John C. Strong, Lindenhurst, IL (US); Mark W. Tubergen, Mount Prospect, IL (US); Russell A. Brierley, West Chester, PA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/375,413

(22) Filed: Feb. 27, 2003

(51) Int. Cl.⁷ .......................................... C07D 498/18
(52) U.S. Cl. ...................................... 540/545
(58) Field of Search ......................... 540/545

(56) References Cited

U.S. PATENT DOCUMENTS 4,877,776 A    10/1989  Murakata et al. .............. 514/43
6,004,801 A    12/1999  Nagamura et al. .......... 435/267

OTHER PUBLICATIONS

Kinugawa et al., "Synthetic process development of antitumor agent KT6587, an indolocarbazole alkaloid K252a derivative", Organic Process Research & Development 3(2):131–134 (1999).

Kase et al., "K–252a, a potent inhibitor of protein kinase c from microbial origin", Journal of Antibiotics 39(8):1059–1066 (1986).

Kino et al., "Practical preparation of K–252a from a fermentation solution", Biosci. Biotechnol. Biochem. 62(8):1627–1629 (1998).

Nakanishi et al., "K–252b, c and d, potent inhibitors of prtein kinase c from microbial origin", Journal of Antibiotics 39(8):1066–1071 (1986).

*Primary Examiner*—Bruck Kifle
(74) *Attorney, Agent, or Firm*—Gregory W. Steele

(57) ABSTRACT

The present invention provides a process for the synthesis of K-252a and intermediates useful in the process.

21 Claims, No Drawings

PREPARATION OF K-252A

TECHNICAL FIELD

The present invention provides a process for the preparation of K-252a and intermediates useful in the process.

BACKGROUND OF THE INVENTION

K-252a (methyl (15S,16R,18R)-16-hydroxy-15-methyl-3-oxo-28-oxa4,14,19-triazaoctacyclo[12.11.2.1$^{15,18}$.0$^{2,6}$.0$^{7,27}$.0$^{8,13}$.0$^{19,26}$.0$^{20,25}$]octacosa-1,6,8,10,12,20,22,24,26-nonaene-16-carboxylate) is a physiologically active substance produced by microorganisms which has demonstrated various pharmacological properties such as the ability to inhibit protein kinase C activity. Previously disclosed methods of isolating K-252a from microorganisms have proven to be inefficient when carried out on large amounts of material and have also been shown to generate the final product in low purity.

Alternatively, crude K-252a can be hydrolyzed to provide K-252b (which is more easily purified) and subsequently alkylated to provide K-252a of high purity. This method has also shown to be impractical for the production of large amounts of material, however, due to the required column chromatography and the use of dimethylsulfate as an alkylating agent, which is highly toxic.

As shown by these examples, there is a continuing need for methods of preparing K-252a of high purity that are amenable to large-scale production. The present invention discloses a preparation of K-252a which eliminates both the need for column chromatography and the use of dimethylsulfate.

SUMMARY OF THE INVENTION

In its principle embodiment, the present invention provides a process for preparing the compound of formula (II)

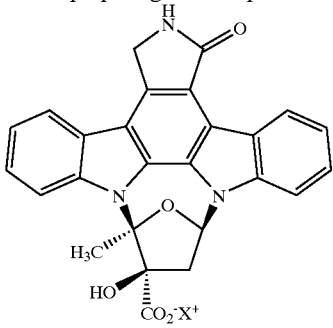

wherein X is selected from the group consisting of Na, NH$_4$, Li, and K; the process comprising:

(a) treating the compound of formula (I)

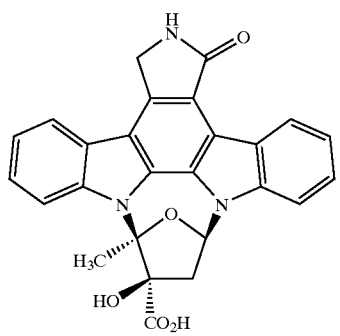

with an aqueous hydroxide base, preferably an aqueous hydroxide base containing up to 25% organic solvent, more preferably an aqueous hydroxide base containing 20% acetone; most preferably aqueous sodium hydroxide or aqueous ammonium hydroxide containing 20% acetone;

(b) crystallizing the product of step (a); and (c) isolating the product of step (b).

In another embodiment, the present invention provides a process for preparing the compound of formula (II), the process comprising:

(a) treating the compound of formula (I) with aqueous sodium hydroxide;

(b) cooling the product of step (a);

(c) optionally partially concentrating the product of step (b); and (d) isolating the product of step (b) or step (c) by filtration.

In another embodiment, the present invention provides a process for preparing the compound of formula (III)

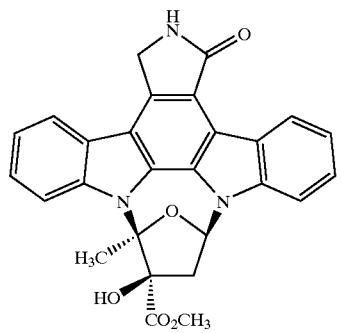

the process comprising:

(a) dissolving the compound of formula (II)

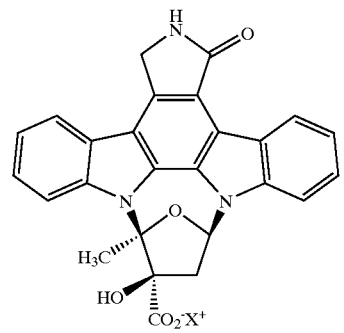

in a solvent, preferably N,N-dimethylacetamide or N,N-dimethylformamide, most preferably N,N-dimethylacetamide;

(b) optionally treating the solution of step (a) with a base, preferably sodium bicarbonate, sodium carbonate, or potassium carbonate, most preferably sodium bicarbonate;

(c) treating the solution of step (a) or step (b) with methyl p-toluenesulfonate; and (d) isolating the product of step (c).

In another embodiment the present invention provides a process for preparing the compound of formula (III)

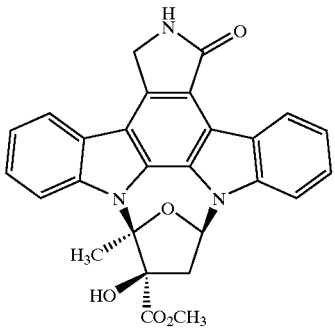

(III), the process comprising:

(a) treating the compound of formula (I)

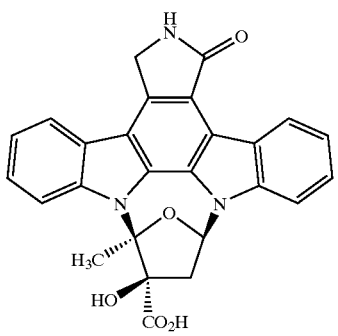

(I), with an aqueous hydroxide base, preferably an aqueous hydroxide base containing up to 25% organic solvent, more preferably an aqueous hydroxide base containing 20% acetone; most preferably aqueous sodium hydroxide or aqueous ammonium hydroxide containing 20% acetone;

(b) crystallizing the product of step (a);

(c) isolating the product of step (b);

(d) dissolving the product of step (c) in a solvent, preferably N,N-dimethylacetamide or N,N-dimethylformamide, most preferably N,N-dimethylacetamide;

(e) optionally treating the solution of step (d) with a base, preferably sodium carbonate, sodium bicarbonate, or potassium carbonate, most preferably sodium bicarbonate; and (f) reacting the product of step (d) or step (e) with a methylating agent, preferably methyl p-toluenesulfonate.

DETAILED DESCRIPTION OF THE INVENTION

The present invention is directed to the preparation of K-252a (methyl (15S,16R,18R)-16-hydroxy-15-methyl-3-oxo-28-oxa-4,14,19-triazaoctacyclo[12.11.2.1$^{15,18}$.0$^{2,6}$.0$^{7,27}$.0$^{8,13}$.0$^{19,26}$.0$^{20,25}$]octacosa-1,6,8,10,12,20,22,24,26-nonaene-16-carboxylate) and to intermediates which are useful in this process. As used in the present specification the following terms have the meanings specified:

The term "aqueous," as used herein, refers to a solution that contains up to 30% organic solvent wherein the remaining solution is water. Preferred aqueous solutions contain up to 25% organic solvent, and more preferred aqueous solutions contain up to 20% organic solvent. Most preferred aqueous solutions contain 20% acetone.

The term "base," as used herein, refers to a reagent capable of accepting protons during the course of a reaction. Examples of bases include carbonate salts such as potassium carbonate, potassium bicarbonate, sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, ammonium hydroxide, and potassium hydroxide; disilylamides such as lithium hexamethyldisilazide, potassium hexamethyldisilazide, and sodium hexamethyldisilazide; trialkylamines such as triethylamine, diisopropylamine, and diisopropylethylamine; heterocyclic amines such as imidazole, pyridine, pyridazine, pyrimidine, and pyrazine; bicyclic amines such as DBN (1,5-diazabicyclo[4.3.0]non-5-ene) and DBU (1,8-diazabicyclo[5.4.0]undec-7-ene); and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "hydroxide base," as used herein, refers to lithium hydroxide, sodium hydroxide, potassium hydroxide, or ammonium hydroxide.

The term "solvent," as used herein, refers to an organic substance that is a liquid at between about 20 and about 35° C. and does not interact with starting materials, reagents, intermediates, or products in a manner which adversely affects the yield of the desired product.

All of the processes of the present invention can be conducted as continuous processes. The term "continuous process," as used herein, represents steps conducted without isolation of the intermediates.

Synthetic Processes

Scheme 1

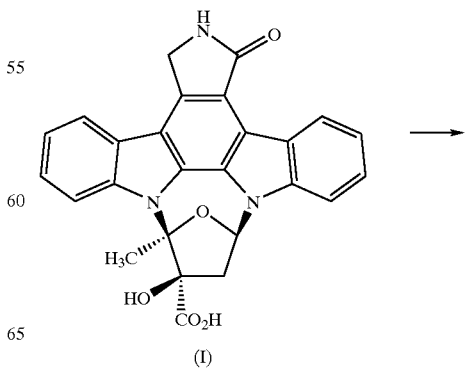

(I)

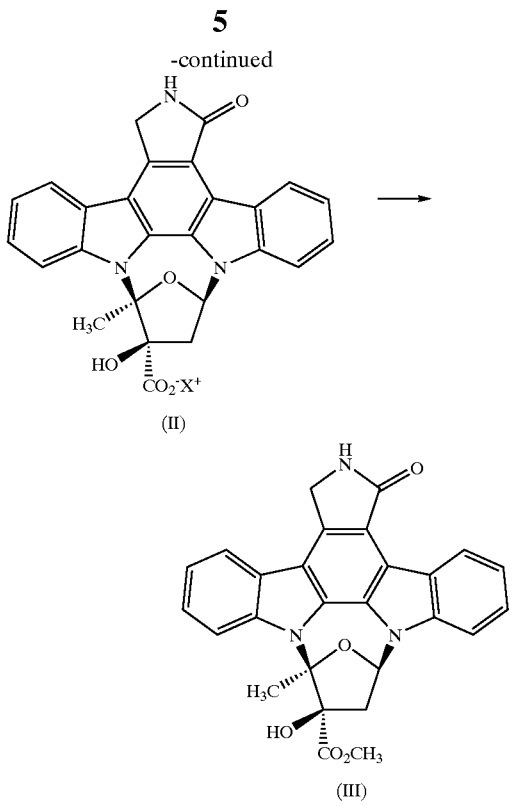

Scheme 1 shows the synthesis of the compound of formula (III) (K-252a). The compound of formula (I) (K-252b; prepared according to a modification of the procedures described in *J. Antibiotics* 1986, 39, 1059–1065 and *Biosci. Biotechnol. Biochem.* 1998, 62, 1627–1629) can be treated with an aqueous hydroxide base to provide the compound of formula (II). Preferably, the aqueous hydroxide is sodium hydroxide or ammonium hydroxide. Examples of solvents used in this reaction include water, acetone, and mixtures thereof. The reaction is typically conducted at temperatures between about 20° C. and about 55° C. (depending on the solvent system used) and then cooled to a temperature of between about −5° C. and about 5° C. to induce crystallization. The resulting crystals are then isolated by filtration to provide the compound of formula (II). Reaction times are typically about 10 to about 24 hours. In a preferred embodiment, the compound of formula (I) is treated with aqueous sodium hydroxide, stirred for one hour at room temperature, treated with acetone, cooled to about 0° C. for about 19 hours, partially concentrated, and filtered to provide the compound of formula (II).

The compound of formula (II) can be converted to the compound of formula (III) (K-252a) by treatment with a methylating agent, preferably methyl p-toluenesulfonate, optionally in the presence of a base (to deprotonate any undesired compound of formula (I) remaining in the reaction). Representative bases used in this reaction include sodium bicarbonate, sodium carbonate, and potassium carbonate. When methyl p-toluenesulfonate is used, sodium acetate is added to decompose any remaining reagent. Examples of solvents used in this reaction include N,N-dimethylacetamide and N,N-dimethylformamide. The preferred solvent is N,N-dimethylacetamide. The reaction is typically conducted at about 35° C. to about 45° C. and then cooled to a temperature of between about 5° C. and about 30° C. Water is added to precipitate the product which is then isolated by filtration to provide the compound of formula (III). Reaction times are typically about 6 to about 12 hours.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects. The contents of all references, patents, and published patent applications cited throughout this application are hereby incorporated by reference.

EXAMPLE 1

Preparation of K-252b Sodium Salt

K-252b (prepared according to the procedures described in *J. Antibiotics* 1986, 39, 1059–1065 and *Biosci. Biotechnol. Biochem.* 1998, 62, 1627–1629;300 L) was concentrated 4-fold using reverse osmosis and then adjusted to pH 3.0 with HCl. The resulting precipitate was isolated by filtration. A sample of the filtered precipitate (506.6 g; 47.6 grams of activity) was crystallized as follows: The sample was treated with 3.5 L of 0.25M NaOH to obtain a concentration of approximately 11–12 g of activity per liter. The mixture was stirred for about an hour at room temperature to form a suspension. The suspension was treated with 700 mL of acetone and the resulting solution was cooled to 0° C. over 6 hours during which time crystals formed. The mixture was held for an additional 13 hours at 0° C. Vacuum was applied with slow stirring to remove the acetone. After acetone removal the solids were filtered and dried over the weekend to produce 25.37 g of the desired product.

EXAMPLE 2

Preparation of K-252b Ammonium Salt

K-252b (prepared according to the procedures described in *J. Antibiotics* 1986, 39, 1059–1065 and *Biosci. Biotechnol. Biochem.* 1998, 62, 1627–1629;300 L) was concentrated 4-fold using reverse osmosis and then adjusted to pH 3.0 with HCl. The resulting precipitate was isolated by filtration. A sample of the filtered precipitate (10.11 g) was crystallized as follows: The sample was treated with 400 mL of 0.3M NH$_4$OH and warmed until the solids were fully dissolved. The resulting solution was refrigerated for 48 hours and filtered. The filter cake was dried under vacuum to provide 316 mg of the desired product (96.4% purity by peak area).

EXAMPLE 3

Alternative Preparation of K-252b Sodium Salt

K-252b (prepared according to the procedures described in *J. Antibiotics* 1986, 39, 1059–1065 and *Biosci. Biotechnol. Biochem.* 1998, 62, 1627–1629;300 L) was concentrated 4-fold using reverse osmosis and then adjusted to pH 3.0 with HCl. The resulting precipitate was isolated by filtration. A sample of the filtered precipitate (150 g; 12.68 g of activity) was crystallized as follows: The sample was added to a reactor containing 1500 mL of 0.25M NaOH. The mixture was heated to about 53° C. until a solution was obtained. The mixture was cooled to 0° C. over 7 hours and held for 13 hours at 0° C. The mixture was filtered and the filter cake was dried to provide 11.3 g (~90% yield at 97.8% purity by peak area) of the desired product.

EXAMPLE 4

Preparation of K-252a From K-252b Sodium Salt

In a 1 L 3-neck jacketed flask fitted with a condenser, a J-kem probe, and an addition funnel was added Example 1 (5 g; 9.78 mmol), sodium bicarbonate (0.55 g; 6.54 mmol), and N,N-dimethylacetamide (23.3 g). The reaction was heated to 40° C., treated with methyl-p-toluenesulfonate (2.36 g, 12.67 mmol); and stirred at 40° C. for about 3 to about 4 hours. The reaction was treated with sodium acetate (1 g), stirred for 4 hours, cooled to room temperature, and treated slowly with water (85 mL). The resulting precipitate was filtered and the filter cake was washed with water (60 mL) and air dried to provide 4.5 g of the desired product.

EXAMPLE 5

Preparation of K-252a From K-252b Ammonium Salt

The desired product can be prepared by substituting Example 2 for Example 1 in Example 4.

What is claimed is:

1. A process for preparing the compound of formula (II)

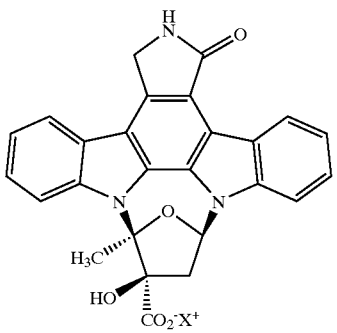

(II), wherein X is selected from the group consisting of Na, NH$_4$, Li, and K;

(a) treating the compound of formula (I)

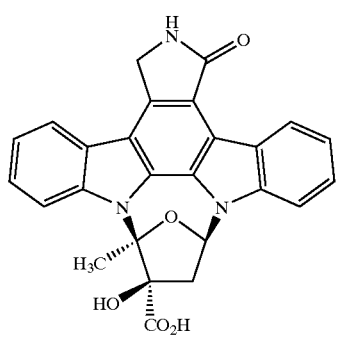

(I), with an aqueous hydroxide base;
(b) crystallizing the product of step (a); and
(c) isolating the product of step (b).

2. The process of claim 1 wherein the aqueous hydroxide base contains up to 25% organic solvent.

3. The process of claim 2 wherein the aqueous hydroxide base contains 20% acetone.

4. The process of claim 3 wherein the aqueous hydroxide base is sodium hydroxide.

5. The process of claim 3 wherein the aqueous hydroxide base is ammonium hydroxide.

6. A process for preparing the compound of formula (II), the process comprising:

(a) treating the compound of formula (I) with aqueous sodium hydroxide;
(b) cooling the product of step (a);
(c) optionally partially concentrating the product of step (b); and
(d) isolating the product of step (b) or step (c) by filtration.

7. A process for preparing the compound of formula (III)

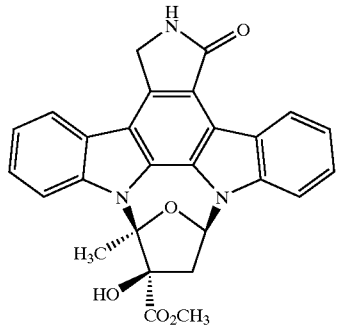

(III), the process comprising:

(a) dissolving the compound of formula (II)

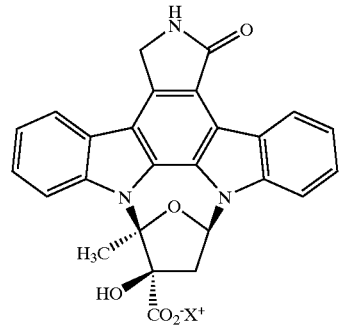

(II), in a solvent;
(b) optionally treating the solution of step (a) with a base;
(c) treating the solution of step (a) or step (b) with methyl p-toluenesulfonate; and
(d) isolating the product of step (c).

8. The process of claim 7 wherein the solvent is selected from the group consisting of N,N-dimethylacetamide and N,N-dimethylformamide.

9. The process of claim 8 wherein the solvent is N,N-dimethylacetamide.

10. The process of claim 7 wherein the base is selected from the group consisting of sodium bicarbonate, sodium carbonate, and potassium carbonate.

11. The process of claim 10 wherein the base is sodium bicarbonate.

12. A process for preparing the compound of formula (III)

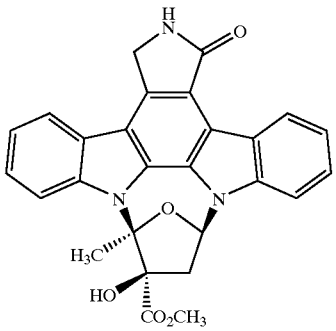

(III), the process comprising:
(a) treating the compound of formula (I)

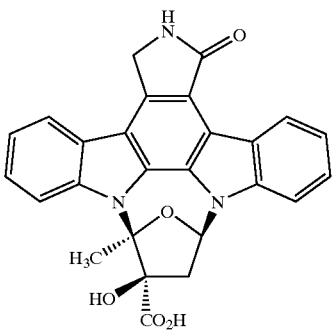

(I), with an aqueous hydroxide base;

(b) crystallizing the product of step (a);

(c) isolating the product of step (b);

(d) dissolving the product of step (e) in a solvent;

(e) optionally treating the solution of step (d) with a base; and (f) reacting the product of step (d) or step (e) with a methylating agent.

13. The process of claim 12 wherein the aqueous hydroxide base contains up to 25% organic solvent.

14. The process of claim 12 wherein the aqueous hydroxide base contains up to 20% acetone.

15. The process of claim 13 wherein the hydroxide base is sodium hydroxide.

16. The process of claim 13 wherein the hydroxide base is ammonium hydroxide.

17. The process of claim 13 wherein the solvent is selected from the group consisting of N,N-dimethylacetamide and N,N,-dimethylformamide.

18. The process of claim 17 wherein the solvent is N,N-dimethylacetamide.

19. The process of claim 13 wherein the base is selected from the group consisting of sodium carbonate, sodium bicarbonate, and potassium carbonate.

20. The process of claim 19 wherein the base is sodium bicarbonate.

21. The process of claim 13 wherein the methylating agent is methyl p-toluenesulfonate.

* * * * *